United States Patent
Mizuno

(10) Patent No.: US 12,138,091 B2
(45) Date of Patent: Nov. 12, 2024

(54) RADIATION IMAGING SYSTEM, RADIATION DETECTOR, CONTROL METHOD FOR RADIATION IMAGING SYSTEM, AND STORAGE MEDIUM

(71) Applicant: CANON KABUSHIKI KAISHA, Tokyo (JP)

(72) Inventor: Tomoyasu Mizuno, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 239 days.

(21) Appl. No.: 18/047,980

(22) Filed: Oct. 19, 2022

(65) Prior Publication Data

US 2023/0130230 A1 Apr. 27, 2023

(30) Foreign Application Priority Data

Oct. 26, 2021 (JP) .................... 2021-174757

(51) Int. Cl.
 *A61B 6/00* (2024.01)
 *A61B 6/42* (2024.01)

(52) U.S. Cl.
 CPC .................... *A61B 6/4208* (2013.01)

(58) Field of Classification Search
 None
 See application file for complete search history.

(56) References Cited

U.S. PATENT DOCUMENTS

| | | | | |
|---|---|---|---|---|
| 2012/0189098 A1* | 7/2012 | Liu | ......... | A61B 6/563 378/62 |
| 2013/0058454 A1* | 3/2013 | Kuwabara | ......... | A61B 6/548 378/62 |
| 2014/0362975 A1* | 12/2014 | Garcia | ......... | A61B 6/4208 378/98.2 |
| 2016/0015341 A1* | 1/2016 | Lee | ......... | A61B 6/548 250/336.1 |

FOREIGN PATENT DOCUMENTS

JP 2017185127 A 10/2017

* cited by examiner

*Primary Examiner* — Hoon K Song
(74) *Attorney, Agent, or Firm* — Canon U.S.A., Inc. IP Division

(57) ABSTRACT

A radiation imaging system includes a radiation detector configured to capture a radiation image based on emitted radiation, a control apparatus configured to control the radiation detector, a radiation generation apparatus configured to emit the radiation, and a plurality of relay apparatuses configured to connect these apparatuses. In the radiation imaging system, the control apparatus performs maintenance of the relay apparatuses via the radiation detector.

12 Claims, 8 Drawing Sheets

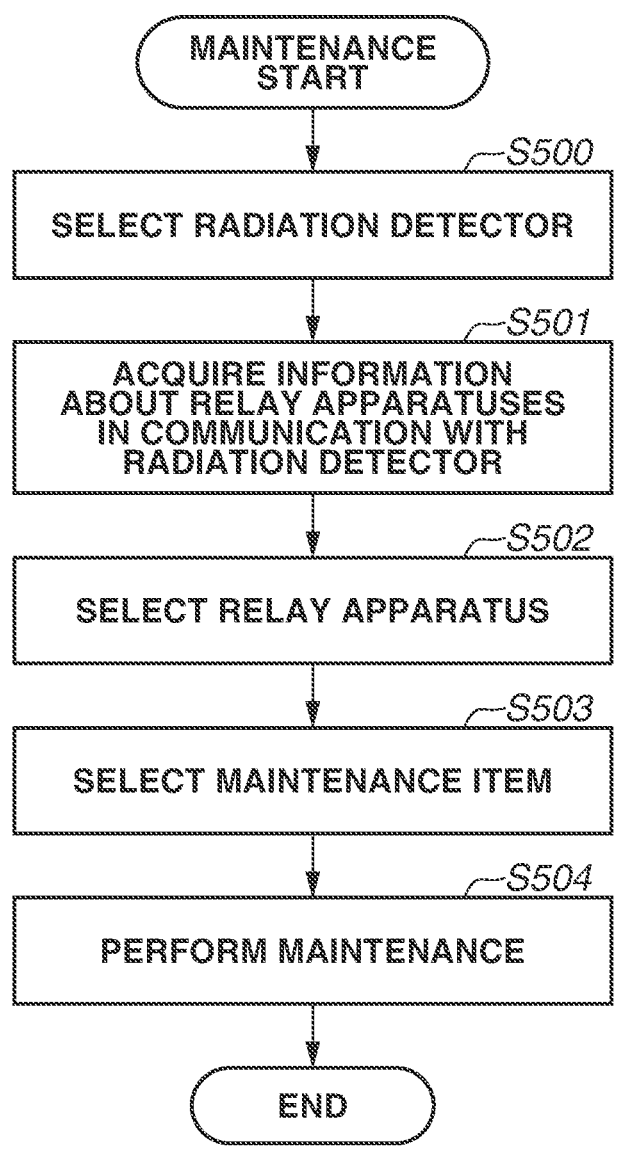

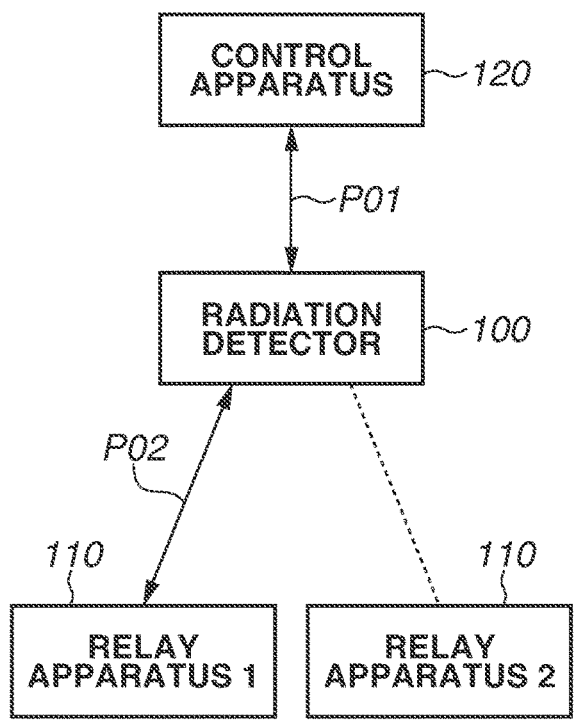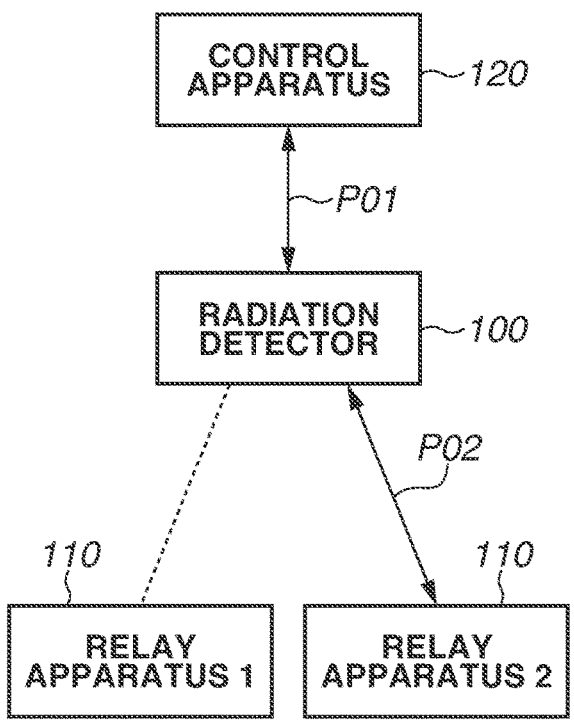

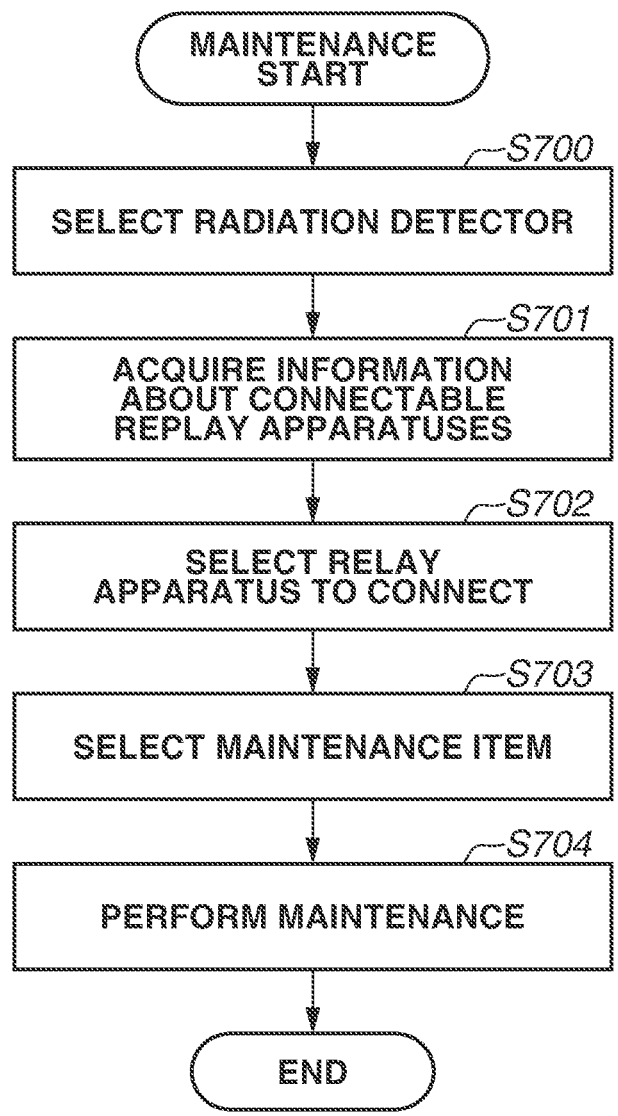

RADIATION IMAGING SYSTEM, RADIATION DETECTOR, CONTROL METHOD FOR RADIATION IMAGING SYSTEM, AND STORAGE MEDIUM

BACKGROUND

Field of the Disclosure

The present disclosure relates to a radiation imaging system, a radiation detector, a method for controlling the radiation imaging system, and a storage medium.

Description of the Related Art

A radiation imaging system using a radiation detector that detects radiation such as an X-ray is widely employed in fields such as industrial use and medical use. Besides the radiation detector, the radiation imaging system includes a radiation generation apparatus and a control terminal having a switch that assists operation of the radiation detector in an imaging room, and a control apparatus such as a personal computer (PC) for controlling the radiation detector to capture an image in an operation room. The radiation imaging system may further include a relay apparatus that relays a connection between such apparatuses. Further, in the imaging room, a plurality of stationary imaging tables for erect imaging and decubitus imaging may be placed, and a plurality of the radiation detectors and/or the relay apparatuses may be installed.

The relay apparatus has a switching hub function of mediating communication between apparatuses, and a function of relaying control between an imaging apparatus and the control terminal and control between the imaging apparatus and the radiation generation apparatus. In recent years, such relay apparatuses have been equipped with further advanced functions such as timing control of each apparatus, and many of the relay apparatuses have a control program and require maintenance. Japanese Patent Application Laid-Open No. 2017-185127 discusses a relay apparatus having a function of calculating a difference between a time at which radiation irradiation is started and a time at which a switch of a control terminal is pressed.

So far, however, much consideration has not been given to a maintenance method in cases other than the configuration in which one relay apparatus is provided in the imaging system like Japanese Patent Application Laid-Open No. 2017-185127, i.e., in cases where a plurality of relay apparatuses is arranged in the imaging system.

Conventionally, for example, a serviceman has directly specified the Internet Protocol (IP) addresses of the plurality of relay apparatuses one by one using the PC to connect to and communicate with the relay apparatuses, and performed maintenance of the relay apparatuses sequentially. This maintenance method may cause an increase in the maintenance man-hours of the serviceman, and also has room for improvement in security of the communication with the relay apparatuses.

SUMMARY

Aspects of the present disclosure provide a maintenance method capable of ensuring secure communication and also reducing man-hours in maintenance of a plurality of relay apparatuses in a system.

According to an aspect of the present disclosure, a radiation imaging system includes a radiation detector configured to capture a radiation image based on radiation emitted from a first radiation source or a second radiation source, a control apparatus configured to control the radiation detector, and a plurality of relay apparatuses including a first relay apparatus configured to connect the radiation detector, the control apparatus, and the first radiation source, and a second relay apparatus configured to connect the radiation detector, the control apparatus, and the second radiation source. The control apparatus connects to the first relay apparatus via the radiation detector in performing maintenance of the first relay apparatus, and connects to the second relay apparatus via the radiation detector in performing maintenance of the second relay apparatus.

Further features of the present disclosure will become apparent from the following description of exemplary embodiments with reference to the attached drawings.

BRIEF DESCRIPTION OF THE DRAWINGS

FIG. 5 is a flowchart illustrating maintenance of the relay apparatus according to a second exemplary embodiment.

FIGS. 6A and 6B are diagrams illustrating apparatus-to-apparatus communication according to a third exemplary embodiment.

FIG. 7 is a flowchart illustrating maintenance of the relay apparatus according to the third exemplary embodiment.

DESCRIPTION OF THE EMBODIMENTS

Figure 1:
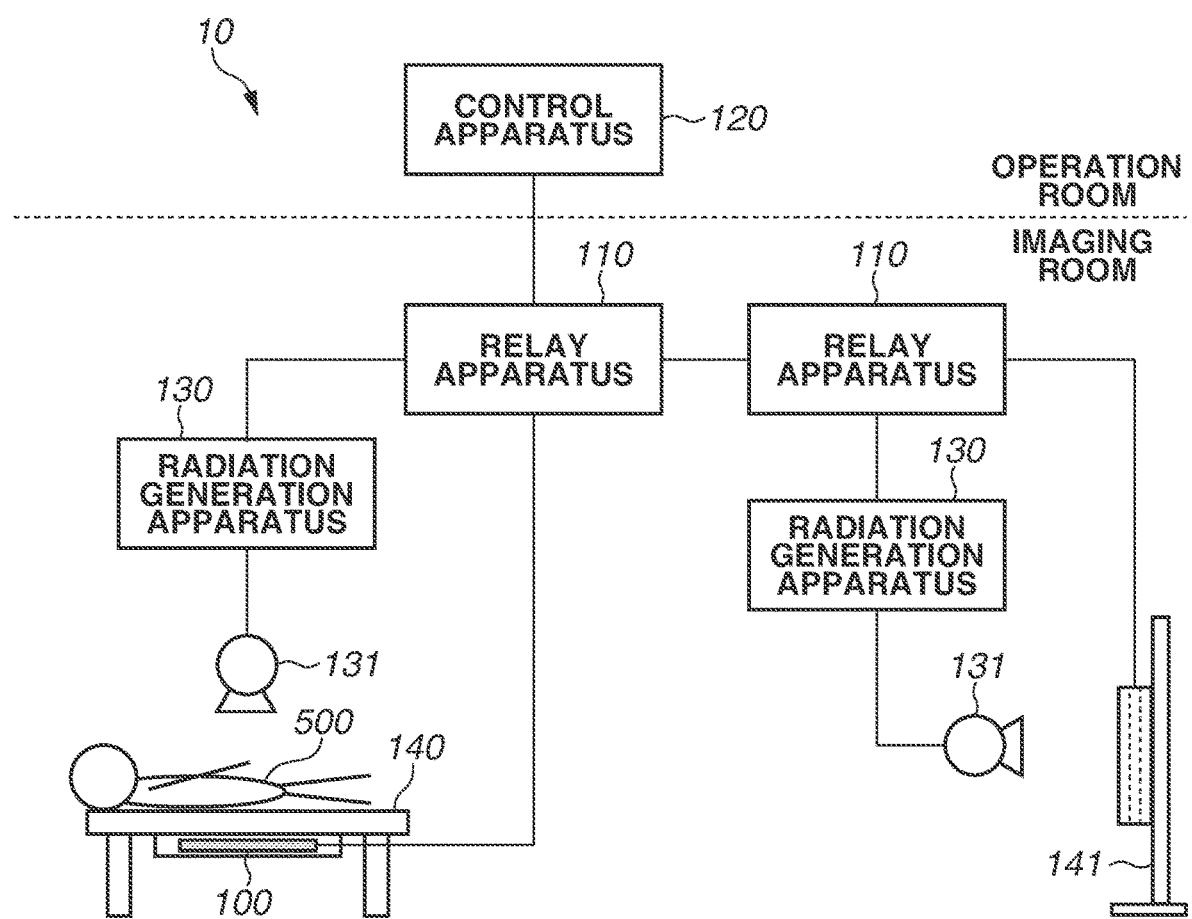
FIG. 1 is a diagram illustrating a radiation imaging system according to a first exemplary embodiment.

Exemplary embodiments of the present disclosure will be described in detail below with reference to the drawings.

Positions and the like of components described in the following exemplary embodiments are arbitrary, and can be changed based on the configuration of an apparatus to which any of the exemplary embodiments is applied or various conditions. Further, through the drawings, the same reference numerals are used to indicate the same or functionally similar elements.

A radiation imaging system according to each of the exemplary embodiments will be described below with reference to the drawings. FIG. 1 illustrates a radiation imaging system 10 according to a first exemplary embodiment.

As illustrated in FIG. 1, the radiation imaging system 10 includes a radiation detector 100, relay apparatuses 110, radiation generation apparatuses 130, radiation sources 131, a decubitus imaging table 140, and an erect imaging table 141 in an imaging room for imaging a subject 500. A control apparatus 120 is placed in an operation room for operating the imaging.

The radiation detector 100 is an apparatus for capturing a radiation image and, for example, includes a flat panel detector (FPD) using an image sensor having two-dimensionally distributed pixels. The image sensor is configured to detect radiation emitted from one of the radiation sources 131 and incident on the image sensor.

The two radiation sources 131 are provided in correspondence with the two imaging tables 140 and 141 illustrated in FIG. 1, but the radiation detector 100 is mounted in one of the two imaging tables 140 and 141 illustrated in FIG. 1 and receives irradiation from one of the radiation sources 131. The radiation detector 100 detects information (dose information) about a two-dimensional distribution of a radiation dose reaching the image sensor, and generates radiation image data.

The radiation detector 100 is communicable with the control apparatus 120 via the corresponding relay apparatus 110. The radiation detector 100 transmits the generated radiation image data to the control apparatus 120 placed in the operation room.

The radiation detector 100 is used in a state of being housed in the decubitus imaging table 140 or the erect imaging table 141 at the time of the imaging. Each of the two imaging tables 140 and 141 functions as a holding unit for holding the radiation detector 100 at an imageable position. The decubitus imaging table 140 for imaging an abdomen or a lower limb and the erect imaging table 141 for imaging a chest are examples of imaging tables. The radiation detector 100 is housed in the decubitus imaging table 140 in FIG. 1, but instead can be attached to the erect imaging table 141 depending on the purpose for imaging.

Each of the relay apparatuses 110 has a switching hub function and is capable of connecting the radiation detector 100, the control apparatus 120, and the radiation generation apparatus 130. Each of the relay apparatuses 110 also has a function of transmitting operation information about the radiation generation apparatus 130 to the radiation detector 100 and relaying information for controlling timings of radiation exposure and detection. Further, a not-illustrated control terminal for controlling power on or off of the radiation detector 100 can be attached to each of the relay apparatuses 110.

The control apparatus 120 acquires information indicating the state of the radiation detector 100 at a predetermined timing, and displays the information on a display or the like to notify a user of the information. Further, the control apparatus 120 includes a graphical user interface (GUI) for operating the radiation detector 100, and this enables the state of the radiation detector 100 to be controlled in the operation room.

Each of the radiation generation apparatuses 130 controls radiation irradiation from the corresponding radiation source 131 under a preset radiation irradiation condition. Pressing of a radiation irradiation switch or control via the GUI using the display or a touch panel is used for the radiation irradiation. Examples of the imaging of the subject 500 include an imaging method that synchronizes the exposure by the radiation generation apparatus 130 and the detection by the radiation detector 100 by transmitting information input via the switch to the radiation detector 100 via the relay apparatus 110 and emitting radiation after receiving from the radiation detector 100 information indicating permission for irradiation.

FIG. 1 illustrates the radiation imaging system 10 having a configuration in which the radiation generation apparatuses 130 control the radiation sources 131 in a one-to-one correspondence, but the radiation imaging system 10 is not limited thereto and may have a configuration in which one radiation generation apparatus 130 controls a plurality of the radiation sources 131.

Mutual communication between the above-described apparatuses may be in compliance with a communication standard such as Recommended Standard 232 version C (RS 232C), Universal Serial Bus (USB), or Ethernet®, or may be communication using a dedicated signal line. Further, the communication may be wired or wireless.

Next, the operation of each apparatus in the imaging using the radiation imaging system 10 will be described.

The user powers on the radiation detector 100 and houses the radiation detector 100 in the decubitus imaging table 140. After the power-on, the radiation detector 100 becomes ready for imaging. The radiation detector 100 takes a predetermined time to transition from a power-off state or a sleep state (an inactive state) to an imaging standby state. Thus, powering on the radiation detector 100 before position adjustment enables the radiation detector 100 to become the imaging standby state during the position adjustment, thereby expediting the imaging.

The user adjusts the positions of the subject 500, the decubitus imaging table 140, and an irradiation region to be irradiated with the radiation from the corresponding radiation source 131. The corresponding radiation generation apparatus 130 controls the radiation source 131 to emit the radiation toward the radiation detector 100 in response to an input via the radiation irradiation switch.

The radiation emitted from the radiation source 131 passes through the subject 500 and is then incident on the radiation detector 100. The radiation detector 100 generates the image data based on the incident radiation and transmits the image data to the control apparatus 120 placed in the operation room. The control apparatus 120 displays the received image data. The operator of the radiation imaging system 10 can check the image displayed on the control apparatus 120 and determine, for example, whether to perform the imaging again.

In a case where the user determines that the displayed image is normal, the user prepares for imaging of another subject 500 by repeating a similar procedure. After completing the imaging of all the subjects 500, the user powers off the radiation detector 100.

Figure 2:
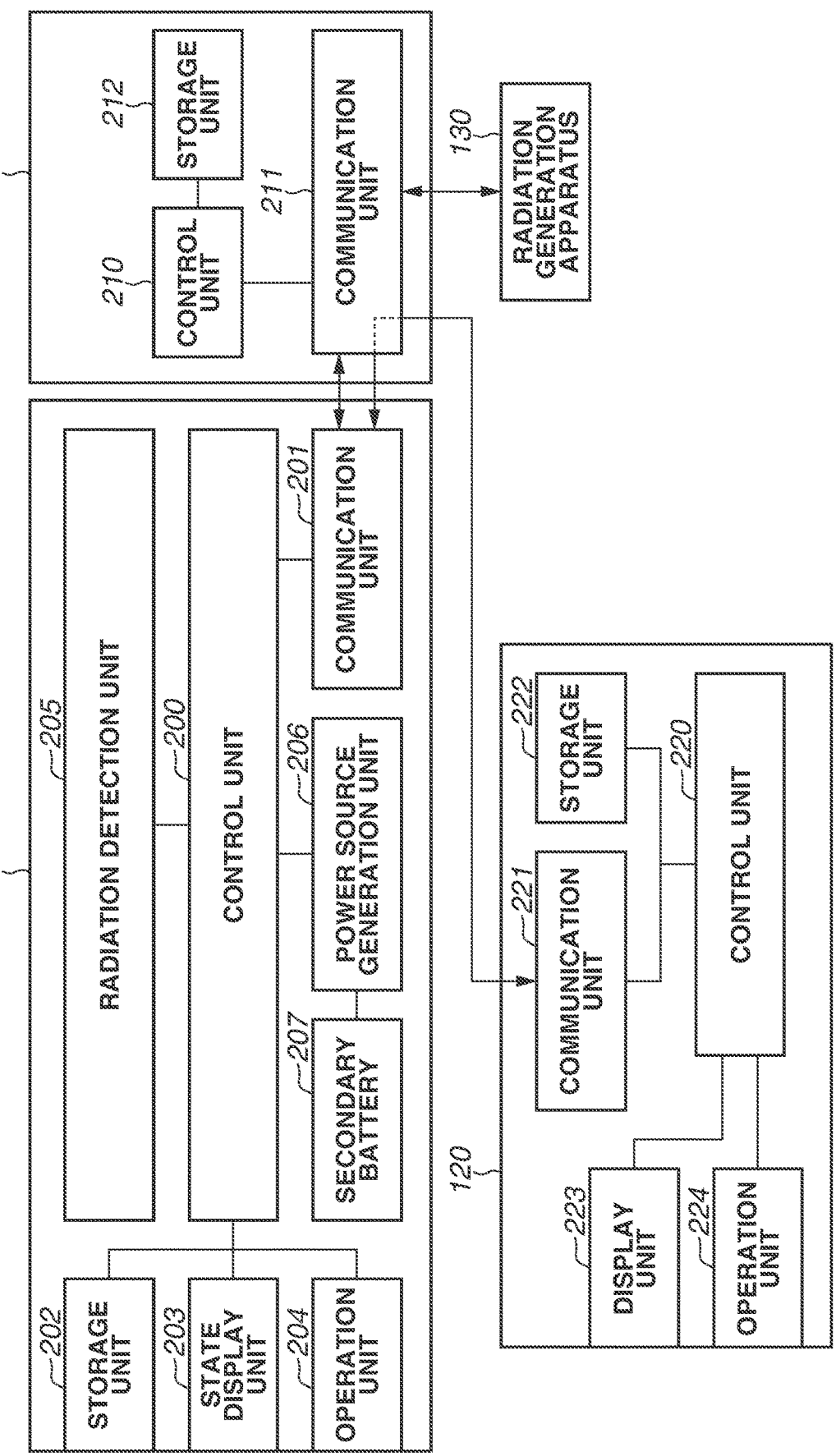
FIG. 2 is a diagram illustrating a radiation detector, a relay apparatus, and a control apparatus according to the first exemplary embodiment.

Next, the radiation detector 100, each of the relay apparatuses 110, and the control apparatus 120 will be described with reference to FIG. 2.

The radiation detector 100 includes a control unit 200, a communication unit 201, a storage unit 202, a state display unit 203, an operation unit 204, a radiation detection unit 205, a power source generation unit 206, and a secondary battery 207.

The control unit 200 performs comprehensive control of the entire radiation detector 100, including driving control of the radiation detection unit 205, digital data correction processing, and control of the communication unit 201. The control unit 200 is formed by a circuit board including, for example, a central processing unit (CPU), a graphics processing unit (GPU), or a field-programmable gate array (FPGA).

The communication unit 201 has a function of performing communication between the radiation detector 100 and another apparatus.

The communication unit 201 transmits and receives various kinds of information to and from another apparatus via wired or wireless communication.

The storage unit 202 can store a control program, image data, a control parameter, and an operation log of the radiation detector 100 therein, and includes a nonvolatile memory. While the nonvolatile memory is described as an example here, the storage unit 202 is not limited thereto and may include a volatile memory.

The state display unit 203 has a function of displaying the state of the radiation detector 100 based on control from the control unit 200. This display enables the operator to recognize the state of the radiation detector 100. For example, the state display unit 203 can display the power state, the driving state, and the wireless communication state of the radiation detector 100 in a recognizable manner.

The operation unit 204 receives an operation from the operator. For example, the operation unit 204 receives information about pressing of a power switch provided for the operator to perform an input operation, and information about an operation on a GUI of the state display unit 203.

The radiation detection unit 205 has a function of detecting the radiation emitted from the radiation source 131 and generating the digital data (the image data) based on the detected radiation.

The power source generation unit 206 generates various kinds of power source voltages and currents for the operation of the radiation detector 100, from power supplied from the secondary battery 207, and supplies the voltages and currents to the respective units.

The secondary battery 207 has a power source function enabling each of the above-described units to operate. The secondary battery 207 may be detachably attached to the radiation detector 100 or built in the radiation detector 100. For example, a lithium ion battery or an electric double layer capacitor can be used as the secondary battery 207.

The control apparatus 120 includes a control unit 220, a communication unit 221, a storage unit 222, a display unit 223, and an operation unit 224.

The control unit 220 has a display control function of controlling display on the display unit 223. Further, the control unit 220 has a function of receiving operation information about the operation unit 224 and displaying the information on the display unit 223, and controls the communication unit 221 that transmits and receives a signal to control the radiation detector 100.

The communication unit 221 has a function of performing communication between the control apparatus 120 and another apparatus.

The communication unit 221 transmits and receives various kinds of information, such as operation information and captured images, to and from another apparatus via wired or wireless communication.

The storage unit 222 can store a control program, captured image data, a control parameter, and an operation log of the control apparatus 120 therein, and includes a nonvolatile memory. While the nonvolatile memory is described as an example here, the storage unit 222 is not limited thereto and may include a volatile memory.

The display unit 223 includes the GUI for operating the radiation detector 100, and enables the GUI to be operated from the operation unit 224.

The relay apparatus 110 includes a control unit 210, a communication unit 211, and a storage unit 212.

The control unit 210 has a function of analyzing data received by the communication unit 211 from the radiation detector 100 or the radiation generation apparatus 130, and transmitting an operation instruction specified in advance by a program to the radiation detector 100 or the radiation generation apparatus 130 based on the analysis result.

The communication unit 211 has a function of performing communication between the relay apparatus 110 and another apparatus. The communication unit 221 transmits and receives various kinds of information, such as operation information and captured images, to and from another apparatus via wired or wireless communication. Further, the communication unit 221 has a switching hub function and mediates the communication between the radiation detector 100 and the control apparatus 120.

The storage unit 212 can store a control program, captured image data, a control parameter, and an operation log of the relay apparatus 110 therein, and includes a nonvolatile memory. While the nonvolatile memory is described as an example here, the storage unit 212 is not limited thereto and may include a volatile memory.

Next, the communication among the communication units 201, 211, and 221 will be described. The communication unit 201 communicates with the communication unit 211 and the communication unit 221. The communication unit 201 and the communication unit 221 communicate with each other via the communication unit 211, but the communication unit 211 operates as a switching hub and simply relays the communication, and, actually, the communication is performed directly between the communication unit 201 and the communication unit 221. Further, the communication unit 211 is connected to the communication unit 221, but data other than relayed data between the communication unit 201 and the communication unit 221 is not transmitted and received between the communication unit 211 and the communication unit 221.

Figure 3:
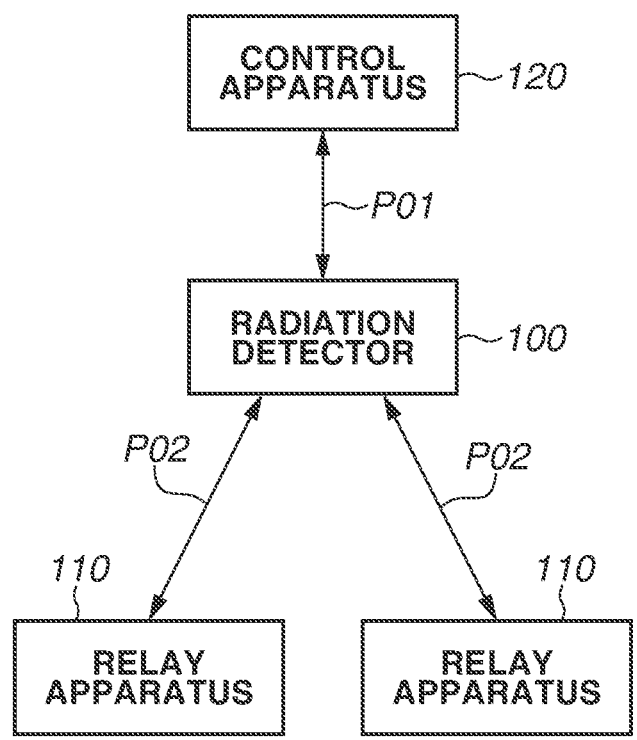
FIG. 3 is a diagram illustrating apparatus-to-apparatus communication according to the first exemplary embodiment.

FIG. 3 illustrates two communication protocols used by the apparatuses in the radiation imaging system 10. The control apparatus 120 communicates with the radiation detector 100 using a control apparatus-to-imaging apparatus protocol P01, which is a first protocol. The control apparatus-to-imaging apparatus protocol P01 is mainly used to transmit the radiation image data from the radiation detector 100 to the control apparatus 120, and transmit and receive operation information about the radiation detector 100 and the control apparatus 120 therebetween.

The radiation detector 100 also communicates with the relay apparatuses 110 using an imaging apparatus-to-relay apparatus protocol P02, which is a second protocol. The imaging apparatus-to-relay apparatus protocol P02 is mainly used to transmit and receive data such as control information directed to apparatuses connected to the relay apparatuses 110, such as the radiation generation apparatuses 130.

The radiation detector 100 communicates with the plurality of relay apparatuses 110 in the radiation imaging system 10 in parallel using the imaging apparatus-to-relay apparatus protocol P02. For example, Transmission Control Protocol/Internet Protocol (TCP/IP) communication is used for the communication between the radiation detector 100 and the relay apparatuses 110.

For example, the radiation detector 100 has a plurality of client task programs for communicating with the relay apparatuses 110. The radiation detector 100 has a client function and establishes the communication by transmitting a connection request to a server function that each of the relay apparatuses 110 has and receiving permission from the server function of each of the relay apparatuses 110. In this manner, the plurality of client tasks in the radiation detector 100 individually and sequentially transmits the connection requests to the respective relay apparatuses 110, thereby establishing the communication with the plurality of relay apparatuses 110.

While the radiation detector 100 is described to communicate with the two relay apparatuses 110 in the radiation imaging system 10 with reference to FIG. 3, the configuration is not limited thereto.

For example, since the number of communications increases or reduces depending on the number of relay apparatuses 110 in the radiation imaging system 10, the radiation detector 100 may communicate with all the relay apparatuses 110 in the radiation imaging system 10, or the relay apparatus 110 that the radiation detector 100 is to communicate with may be set in the radiation detector 100 and the radiation detector 100 may communicate with the set relay apparatus 110. The relay apparatus 110 that the radiation detector 100 is to communicate with may be set in the radiation detector 100 in advance, or may be set from the control apparatus 120 using the control apparatus-to-imaging apparatus protocol P01.

Each of the relay apparatuses 110 has a control program in order to transmit and receive various kinds of information to and from the corresponding radiation generation apparatus 130 and the radiation detector 100 and issue a control instruction to each of the apparatuses. The storage unit 212 of each of the relay apparatuses 110 stores the control program, the operation log, the operation setting parameter, and the like therein. A serviceman performs maintenance of the relay apparatuses 110, for example by writing the control program, acquiring the operation log, or writing the operation setting parameter during the maintenance. The maintenance is not limited thereto, and may include failure diagnosis, calibration, or the like of the relay apparatus 110.

The maintenance of the relay apparatuses 110 is performed using the GUI on the display unit 223 of the control apparatus 120. The maintenance of the relay apparatuses 110 is performed from the control apparatus 120 via the radiation detector 100. The control apparatus-to-imaging apparatus protocol P01 and the imaging apparatus-to-relay apparatus protocol P02 described with reference to FIG. 3 are used in the communication from the control apparatus 120 to the relay apparatus 110. More specifically, for example, in the case of writing the control program, data of the program selected on the control apparatus 120 is transmitted to the radiation detector 100 first and then the radiation detector 100, which has received the data, transmits the data to the relay apparatus 110.

Because the control apparatus-to-imaging apparatus protocol P01 is a communication route used to image the subject 500 in the radiation imaging system 10, a more secure design is employed therefor to prevent a leak of image information and image alternation. Further, because the communication using the imaging apparatus-to-relay apparatus protocol P02 is used to issue a control instruction to the radiation generation apparatus 130, a secure design is also employed therefor. Thus, using this communication route also in the maintenance is a method advantageous in terms of security such as a countermeasure against program alteration.

Figure 4:
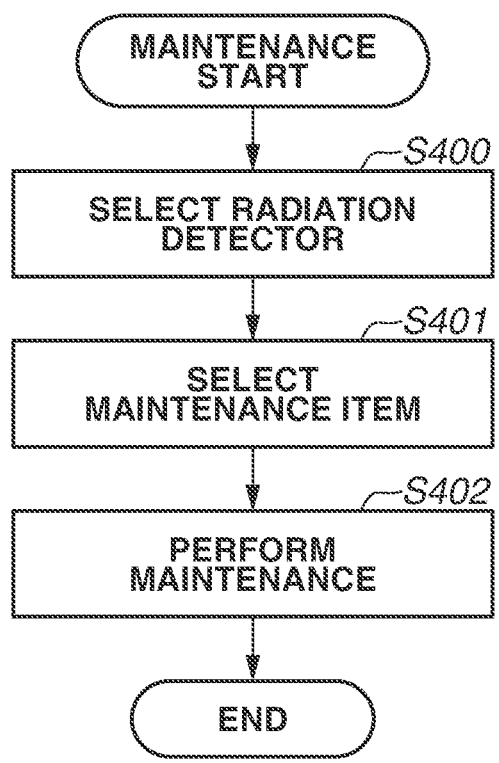
FIG. 4 is a flowchart illustrating maintenance of the relay apparatus according to the first exemplary embodiment.

Next, a procedure for the maintenance of the relay apparatuses 110 will be described with reference to FIG. 4.

In step S400, a maintainer such as the serviceman selects the radiation detector 100 to be used to relay the maintenance of the relay apparatuses 110, on the GUI of the control apparatus 120. While in the present exemplary embodiment, the radiation imaging system 10 is described to include one radiation detector 100 with reference to FIG. 1, the radiation imaging system 10 may include a plurality of the radiation detectors 100 and step S400 is to be performed in this case.

In step S401, the maintainer selects a maintenance item on the GUI of the control apparatus 120. The maintenance item can be selected from control program writing, operation log acquisition, and operation setting parameter setting/acquisition. When the control program writing or the operation setting parameter setting is selected, the maintainer selects a file to transmit in this step.

In step S402, the maintainer issues a maintenance execution instruction via the GUI of the control apparatus 120.

Performing the above-described procedure enables the maintainer to perform the maintenance of all the relay apparatuses 110 in communication with the radiation detector 100 by issuing the maintenance execution instruction once.

For example, in the case of the control program writing, the control program is written into all the relay apparatuses 110 in communication with the radiation detector 100 selected in step S400. In the example of FIG. 1, the control program in each of the two relay apparatuses 110 is overwritten with the program in the file selected in step S401.

For example, in the case of the operation log acquisition, the operation logs are acquired from all the relay apparatuses 110 in communication with the radiation detector 100 selected in step S400. In the example of FIG. 1, the operation log of each of the two relay apparatuses 110 is acquired. In the operation log acquisition, files as many as the number of relay apparatuses 110 may be able to be acquired, or the operation logs may be organized into one file by the radiation detector 100 or the control apparatus 120 and be output as the file. The same also applies to the case of the operation setting parameter acquisition.

For example, in the case of the operation setting parameter setting, the operation setting parameter is written into all the relay apparatuses 110 in communication with the radiation detector 100 selected in step S400. In the example of FIG. 1, the operation setting parameter of each of the two relay apparatuses 110 is overwritten with the operation setting parameter in the file selected in step S401.

As described above, according to the present exemplary embodiment, the control apparatus 120 performs the maintenance of the relay apparatuses 110 via the radiation detector 100, and therefore secure maintenance is ensured. Further, the radiation detector 100 communicates with the plurality of relay apparatuses 110 in parallel, and this enables the maintainer to perform the maintenance of the plurality of relay apparatuses 110 simultaneously by performing the procedure once, thereby reducing the man-hours.

In the first exemplary embodiment, the method that connects the plurality of relay apparatuses 110 in the radiation imaging system 10 to the radiation detector 100 to communicate therewith and performs the maintenance of all the relay apparatuses 110 in communication with the radiation detector 100 by performing the procedure once, thereby ensuring secure maintenance and also enabling the maintainer to easily perform the maintenance has been described. In a second exemplary embodiment, a method that enables the maintainer to select a relay apparatus from among the plurality of relay apparatuses 110 in the radiation imaging system 10 and to perform the maintenance of the selected relay apparatus will be described.

The maintenance of the selected relay apparatus can be implemented by selecting the relay apparatus on the GUI of the control apparatus 120 in the maintenance procedure with the configuration according to the first exemplary embodiment. A procedure for the maintenance will be described with reference to FIG. 5.

In step S500, the maintainer selects the radiation detector 100 to be used to relay the maintenance of the relay apparatuses 110, on the GUI of the control apparatus 120. The radiation imaging system 10 is described to include one radiation detector 100 with reference to FIG. 1 in the first exemplary embodiment, but may include a plurality of the radiation detectors 100, and step S500 is to be performed in this case.

In step S501, the control apparatus 120 acquires information about the relay apparatuses 110 in communication with the radiation detector 100, from the radiation detector 100. In a case where the control apparatus 120 has already held this information, such as a case where the control apparatus 120 sets the relay apparatus 110 to communicate with the radiation detector 100, step S501 can be skipped.

In step S502, the maintainer selects the relay apparatus 110 as the maintenance target, from among the relay apparatuses 110 in communication with the radiation detector 100 based on the information acquired in or before step S501, using the GUI of the control apparatus 120.

In step S503, the maintainer selects a maintenance item on the GUI of the control apparatus 120. Maintenance item options are similar to those described in the first exemplary embodiment.

In step S504, the maintainer issues a maintenance execution instruction via the GUI of the control apparatus 120.

Performing the above-described procedure enables the maintainer to select the relay apparatus 110 as the maintenance target, from among the relay apparatuses 110 in communication with the radiation detector 100, and perform the maintenance of the selected relay apparatus 110.

As described above, according to the present exemplary embodiment, the maintainer can perform the maintenance of the relay apparatus 110 selected from among the relay apparatuses 110 that the radiation detector 100 is in communication with. Being able to select the relay apparatus 110 as the maintenance target, for example, being able to select only the relay apparatus 110 in which a trouble has occurred to perform the maintenance thereof enables further reduction of maintenance man-hours compared to the first exemplary embodiment depending on the state of the radiation imaging system 10.

In the first and second exemplary embodiments, the method in which the radiation detector 100 in the radiation imaging system 10 connects to the plurality of relay apparatuses 110 and establishes communication therewith, thereby enabling the maintainer to easily perform the maintenance. In a third exemplary embodiment, a method that enables the maintainer to select one relay apparatus to connect to and establish communication with, from among the plurality of relay apparatuses 110 in the radiation imaging system 10, and to perform the maintenance of the selected relay apparatus.

The maintenance by selecting the relay apparatus to communicate with can be implemented by selecting the relay apparatus to communicate with in the imaging apparatus-to-relay apparatus communication in the configuration according to the first exemplary embodiment. FIGS. 6A and 6B illustrate a concept of this communication.

The control apparatus-to-imaging apparatus protocol P01 and the imaging apparatus-to-relay apparatus protocol P02 are similar to those in the first exemplary embodiment. The radiation detector 100 communicates with one relay apparatus 110 in the radiation imaging system 10 using the imaging apparatus-to-relay apparatus protocol P02, and can change the relay apparatus 110 to communicate with as illustrated in FIGS. 6A and 6B. The relay apparatus 110 that the radiation detector 100 is to communicate with may be set in the radiation detector 100 in advance, or may be set from the control apparatus 120 using the control apparatus-to-imaging apparatus protocol P01.

Next, a procedure for the maintenance of the relay apparatus 110 will be described with reference to FIG. 7.

In step S700, the maintainer selects the radiation detector 100 to be used to relay the maintenance of the relay apparatus 110, on the GUI of the control apparatus 120. The radiation imaging system 10 is described to include one radiation detector 100 with reference to FIG. 1 in the first exemplary embodiment, but may include a plurality of the radiation detectors 100, and step S700 is to be performed in this case.

In step S701, the control apparatus 120 acquires information about the relay apparatuses 110 communicable with the radiation detector 100, from the radiation detector 100. In a case where the control apparatus 120 has already held this information, step S701 can be skipped.

In step S702, the maintainer selects the relay apparatus 110 to communicate with, from among the relay apparatuses 110 communicable with the radiation detector 100 based on the information acquired in or before step S701, using the GUI of the control apparatus 120. The relay apparatus 110 selected at this time is the relay apparatus of which maintenance can be performed from the control apparatus 120.

In step S703, the maintainer selects a maintenance item on the GUI of the control apparatus 120. Maintenance item options are similar to those described in the first exemplary embodiment.

In step S704, the maintainer issues a maintenance execution instruction via the GUI of the control apparatus 120.

Performing the above-described procedure enables the maintainer to select the relay apparatus 110 to communicate with the radiation detector 100 and perform the maintenance of the selected relay apparatus 110.

As described above, according to the present exemplary embodiment, the maintainer can select the relay apparatus 110 as the maintenance target, and reduce the man-hours by, for example, performing the maintenance of only the relay apparatus 110 in which a trouble has occurred.

Figure 8:
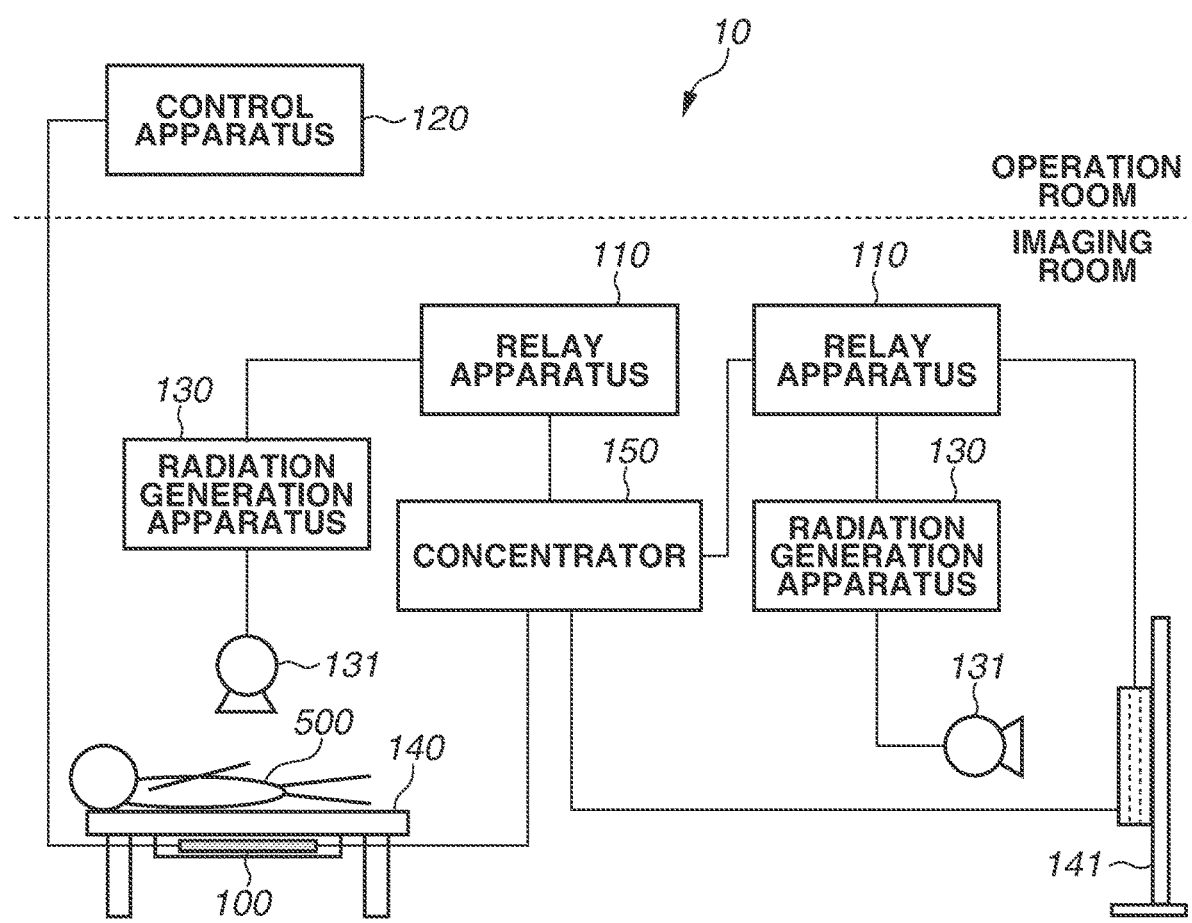
FIG. 8 is a diagram illustrating an example of a radiation imaging system including a concentrator.

The configuration of the radiation imaging system 10 according to the above-described exemplary embodiments is merely an example, and the radiation imaging system 10 is not limited thereto. For example, while the radiation imaging system 10 has the configuration in which the relay apparatuses 110 each have a switching hub function and are connected to each other in a cascade manner in FIG. 1, a concentrator 150 having a switching hub function may be additionally provided (refer to FIG. 8). Further alternatively, the radiation imaging system 10 may have a configuration in which the control apparatus 120 directly connects to the radiation detector 100, not via the relay apparatus 110 (refer to FIG. 8).

Each of the above-described exemplary embodiments of the present disclosure merely indicates an example of how to embody the present disclosure when implementing the present disclosure, and the technical scope of the present disclosure shall not be construed limitedly by these exemplary embodiments. Modifications, improvements, and the like appropriately made to the above-described exemplary embodiments based on ordinary knowledge of those skilled in the art without departing from the technical idea of the present disclosure or the main features thereof also fall within the scope of the present disclosure.

According to the exemplary embodiments of the present disclosure, it is possible to ensure secure communication and also reduce man-hours in maintenance of a plurality of relay apparatuses in a system.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of priority from Japanese Patent Application No. 2021-174757, filed Oct. 26, 2021, which is hereby incorporated by reference herein in its entirety.

What is claimed is:

1. A radiation imaging system comprising:
   a radiation detector configured to capture a radiation image based on radiation emitted from a first radiation source or a second radiation source;
   a control apparatus configured to control the radiation detector; and
   a plurality of relay apparatuses including a first relay apparatus configured to connect the radiation detector, the control apparatus, and the first radiation source, and a second relay apparatus configured to connect the radiation detector, the control apparatus, and the second radiation source,
   wherein the control apparatus connects to the first relay apparatus via the radiation detector in performing maintenance of the first relay apparatus, and connects to the second relay apparatus via the radiation detector in performing maintenance of the second relay apparatus.

2. The radiation imaging system according to claim 1, wherein, in performing the maintenance, the control apparatus communicates with the radiation detector using a first protocol for transmitting the radiation image from the radiation detector to the control apparatus, and
   wherein, in performing the maintenance, the plurality of relay apparatuses communicates with the radiation detector using a second protocol for transmitting and receiving data to and from an apparatus connected to at least one of the plurality of relay apparatuses.

3. The radiation imaging system according to claim 1, wherein the control apparatus specifies at least one relay apparatus among the plurality of relay apparatuses connected via the radiation detector and performs the maintenance of the at least one relay apparatus.

4. The radiation imaging system according to claim 1, wherein the control apparatus specifies two or more relay apparatuses among the plurality of relay apparatuses connected via the radiation detector and performs the maintenance of the two or more relay apparatuses in parallel.

5. The radiation imaging system according to claim 1, wherein the control apparatus acquires an operation log of at least one relay apparatus among the plurality of relay apparatuses during the maintenance.

6. The radiation imaging system according to claim 1, wherein the control apparatus acquires operation logs of two or more relay apparatuses among the plurality of relay apparatuses in parallel during the maintenance.

7. The radiation imaging system according to claim 1, wherein the control apparatus writes, into at least one relay apparatus among the plurality of relay apparatuses, a control program for controlling the at least one relay apparatus during the maintenance.

8. The radiation imaging system according to claim 1, wherein the control apparatus writes in parallel, into two or more relay apparatuses among the plurality of relay apparatuses, a control program for controlling the two or more relay apparatuses during the maintenance.

9. The radiation imaging system according to claim 1, wherein the plurality of relay apparatuses is connected to each other.

10. A radiation detector included in a radiation imaging system and configured to capture a radiation image based on radiation emitted from a first radiation source or a second radiation source, the radiation imaging system further including a control apparatus configured to control the radiation detector, and a plurality of relay apparatuses including a first relay apparatus configured to connect the radiation detector, the control apparatus, and the first radiation source, and a second relay apparatus configured to connect the radiation detector, the control apparatus, and the second radiation source,
    wherein the radiation detector is connected between the control apparatus and the first relay apparatus in a case where maintenance of the first relay apparatus is performed by the control apparatus, and is connected between the control apparatus and the second relay apparatus in a case where maintenance of the second relay apparatus is performed by the control apparatus.

11. A method for controlling a radiation imaging system including a radiation detector configured to capture a radiation image based on radiation emitted from a first radiation source or a second radiation source, a control apparatus configured to control the radiation detector, and a plurality of relay apparatuses including a first relay apparatus configured to connect the radiation detector, the control apparatus, and the first radiation source, and a second relay apparatus configured to connect the radiation detector, the control apparatus, and the second radiation source, the method comprising:
    causing the control apparatus to connect to the first relay apparatus via the radiation detector to perform maintenance of the first relay apparatus; and
    causing the control apparatus to connect to the second relay apparatus via the radiation detector to perform maintenance of the second relay apparatus.

12. A non-transitory computer-readable storage medium storing a program for causing a computer to perform the method according to claim 11.

* * * * *